United States Patent
Masson et al.

(10) Patent No.: US 9,561,246 B2
(45) Date of Patent: Feb. 7, 2017

(54) USE OF ODIPARCIL IN THE TREATMENT OF A MUCOPOLYSACCHARIDOSIS

(71) Applicant: Inventiva, Daix (FR)

(72) Inventors: Philippe Masson, Hauteville-les-Dijon (FR); Jean-Louis Junien, Sevres (FR)

(73) Assignee: Inventiva, Daix (FR)

( * ) Notice: Subject to any disclaimer, the term of this patent is extended or adjusted under 35 U.S.C. 154(b) by 0 days.

(21) Appl. No.: 14/506,239

(22) Filed: Oct. 3, 2014

(65) Prior Publication Data

US 2015/0099789 A1     Apr. 9, 2015

(30) Foreign Application Priority Data

Oct. 4, 2013  (FR) ..................... 13 59657

(51) Int. Cl.
*A61K 31/7048* (2006.01)
*A61K 9/20* (2006.01)

(52) U.S. Cl.
CPC ......... *A61K 31/7048* (2013.01); *A61K 9/2027* (2013.01); *A61K 9/2054* (2013.01)

(58) Field of Classification Search
None
See application file for complete search history.

(56) References Cited

U.S. PATENT DOCUMENTS 5,169,838 A    12/1992   Samreth et al.

FOREIGN PATENT DOCUMENTS

EP    0 421 829 A1    4/1991

OTHER PUBLICATIONS

Harmatz et al. in Journal of Pediatrics 2006;148:533-539.*
Meyers et al. in the Journal of Clinical Pharmacology 2008;48:1158-1170.*
Schuchman et al. in Plos One 8(1): e54459 (published: Jan. 24, 2013).*
Weinstein et al. Connective Tissue Research Early Online: 1-11 (2011).*
Myers et al., "Characterization of Total Plasma Glycosaminoglycan Levels in Healthy Volunteers Following Oral Administration of a Novel Antithrombotic Odiparcil with Aspirin or Enoxaparin," Journal of Clinical Pharmacology, vol. 48, No. 10, Oct. 10, 2008, pp. 1158-1170, XP002719465.
European Search Report dated Jan. 30, 2014 with partial translation (Three (3) pages).
Elizabeth F. Neufeld et al., "The Mucopolysaccharidoses", The Metabolic Basis of Inherited Diseases, 1989, Sixth Edition, Chapter 61, pp. 1565-1587, McGraw-Hill Information Services Company, New York, USA.
Talia Weinstein et al., β-D-Xylosides Stimulate GAG Synthesis in Chondrocyte Cultures Due to Elevation of the Extracellular GAG Domains, Accompanied by the Depletion of the Intra-pericellular GAG Pools, with Alterations in the GAG Profiles, Connective Tissue Research, Early Online: 1-11, 2011.

* cited by examiner

*Primary Examiner* — Dennis Heyer
(74) *Attorney, Agent, or Firm* — Crowell & Moring LLP

(57) ABSTRACT

The present invention relates to a method of treatment of a mucopolysaccharidosis with 4-methyl-2-oxo-2H-1-benzopyran-7-yl-5-thio-β-D-xylopyranoside.

11 Claims, 1 Drawing Sheet

USE OF ODIPARCIL IN THE TREATMENT OF A MUCOPOLYSACCHARIDOSIS

Figure 1:
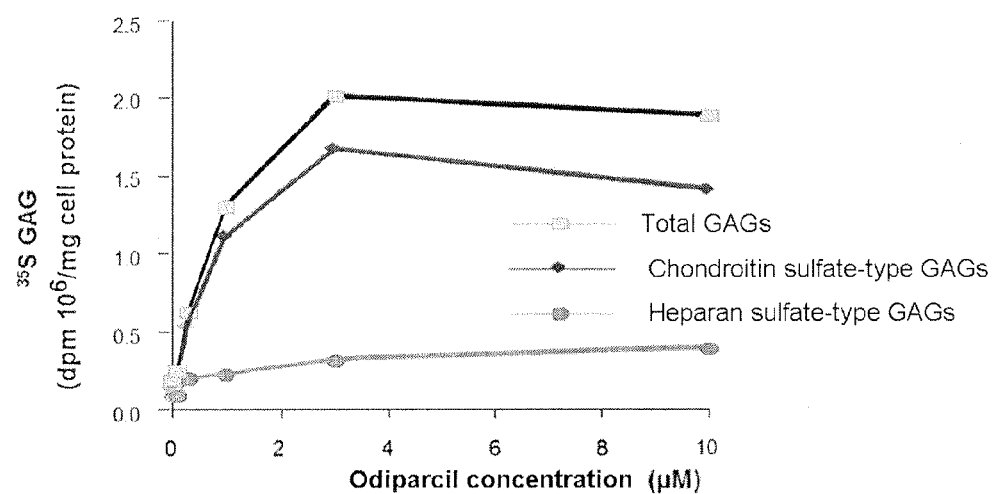

The present invention relates to the use of Odiparcil, or of a pharmaceutical composition containing this compound, in the treatment of a mucopolysaccharidosis, and in particular of Maroteaux-Lamy disease.

TECHNICAL BACKGROUND OF THE INVENTION

Mucopolysaccharidoses (MPSs) are degenerative genetic diseases linked to an enzymatic defect. In particular, MPSs are caused by the deficiency or the inactivity of lysosomal enzymes which catalyze the gradual metabolism of complex sugar molecules called glycosaminoglycans (GAGs). These enzymatic deficiencies cause an accumulation of GAGs in the cells, the tissues and, in particular, the cell lysosomes of affected subjects, leading to permanent and progressive cell damage which affects the appearance, the physical capacities, the organ function and, in most cases, the mental development of affected subjects.

Eleven distinct enzymatic defects have been identified, corresponding to seven distinct clinical categories of MPS. Each MPS is characterized by a deficiency or inactivity of one or more enzymes which degrade mucopolysaccharides, namely heparan sulfate, dermatan sulfate, chondroitin sulfate and keratin sulfate.

Mucopolysaccharidosis type III (MPS III) or Sanfilippo disease is a lysosomal storage disease, of the mucopolysaccharidosis group, characterized by severe and rapid intellectual degradation. The first symptoms appear between 2 and 6 years old: behavioral problems (hyperkinesia, aggressiveness) and intellectual degradation, and sleeping problems with very moderate dysmorphic signs. The neurological damage becomes more marked around the age of 10 years old, with loss of psychomotor acquisitions and of communication with the entourage. Epilepsy often occurs after the age of 10 years old. The disease is due to the presence of undegraded heparan sulfate owing to the defect in one or other of the four enzymes required for its catabolism, responsible for one of the four types of MPS III: type IIIA (heparan sulfamidase), type IIIB (alpha-N-acetylglucosaminidase), type IIIC (acetylCoA: alpha-glucosaminide-N-acetyltransferase) and type IIID (N-acetylglucosamine-6-sulfate sulfatase). There is at the current time no effective treatment for this disease.

Mucopolysaccharidosis type VI (MPS VI) or Maroteaux-Lamy disease is a lysosomal storage disease, of the mucopolysaccharidosis group, characterized by severe somatic involvement and an absence of psycho-intellectual regression. The prevalence of this rare mucopolysaccharidosis is between 1/250 000 and 1/600 000 births. In the severe forms, the first clinical manifestations occur between 6 and 24 months and are gradually accentuated: facial dysmorphia (macroglossia, mouth constantly half open, thick features), joint limitations, very severe dysostosis multiplex (platyspondyly, kyphosis, scoliosis, pectus carinatum, genu valgum, long bone deformation), small size (less than 1.10 m), hepatomegaly, heart valve damage, cardiomyopathy, deafness, corneal opacities. Intellectual development is usually normal or virtually normal, but the auditory and ophthalmological damage can cause learning difficulties.

The symptoms and the severity of the disease vary considerably from one patient to the other and intermediate forms, or even very moderate forms also exist (spondyloepiphyseal-metaphyseal dysplasia associated with cardiovascular involvement). Like the other mucopolysaccharidoses, Maroteaux-Lamy disease is linked to the defect of an enzyme of mucopolysaccharide metabolism, in the case in point N-acetylgalactosamine-4-sulfatase (also called arylsulfatase B). This enzyme metabolizes the sulfate group of dermatan sulfate (Neufeld et al.: "The mucopolysaccharidoses" The Metabolic Basis of Inherited Diseases, eds. Scriver et al, New York, McGraw-Hill, 1989, p. 1565-1587). This enzymatic defect blocks the gradual degradation of dermatan sulfate, thereby leading to an accumulation of dermatan sulfate in the lysosomes of the storage tissues. At the current time, there is just one medicament authorized for the treatment of this disease: Naglazyme® (recombinant human galsulfase), the cost of which is extremely high (in the United States, it is about $350 000 per year). An alternative to this treatment is bone marrow allograft.

Mucopolysaccharidosis type VII (MPS VII) or Sly disease is a very rare lysosomal storage disease of the mucopolysaccharidosis group. The symptomology is extremely heterogeneous: antenatal forms (nonimmune fetoplacental anasarca), severe neonatal forms (with dysmorphia, hernias, hepatosplenomegaly, club feet, dysostosis, significant hypotonia and neurological problems evolving to retarded growth and a profound intellectual deficiency in the event of survival) and very moderate forms discovered at adolescence or even at adult age (thoracic kyphosis). The disease is due to a defect in beta-D-glucuronidase, responsible for accumulation, in the lysosomes, of various glycosaminoglycans: dermatan sulfate, heparan sulfate and chondroitin sulfate. There is at the current time no effective treatment for this disease.

There is therefore clearly a need to provide subjects suffering from MPS type III, VI and VII with a drug treatment, and in the case of MPS type VI, an alternative treatment not derived from biotechnology.

Odiparcil (4-methyl-2-oxo-2H-1-benzopyran-7-yl-5-thio-β-D-xylopyranoside; CAS 137215-12-4) belongs to the thioxyloside family. This compound, described in patent application EP-A-0 421 829, corresponds to the formula:

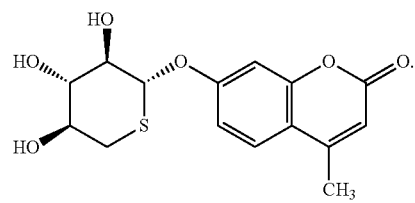 [SMILES: Cc1cc(=O)oc2cc(O[C@@H]3SC[C@@H](O)[C@H](O)[C@H]3O)ccc12]

This compound was the subject of a clinical development (phases 1 and 2) in the treatment of thrombosis at the end of the 1990s and at the beginning of the 2000s. Its mechanism of action can be summarized in the following way: Odiparcil behaves as a substrate for an enzyme, GT1 (galactosyl transferase 1), which initiates the synthesis of GAG chains toward the dermatan sulfate/chondroitin sulfate pathway. These GAGs are cell constituents as proteoglycans (when they are bonded to proteins on a serine and a first sugar which is xylose) and are also secreted into the extracellular medium. They have varied roles, ranging from the control of coagulation (heparin/heparan and dermatan sulfate secreted into the circulation) to the regulation of growth factors (beta-glycan).

It has now been noted, and this is the subject of the present invention, that Odiparcil makes it possible to increase total GAG synthesis at the extracellular level and, by the same token, will contribute to reducing the intracellular GAG load by acting as a "decoy", making the residual activity of N-acetylgalactosamine-4-sulfatase more effective. It is thus possible to envision the treatment of MPS type III, VI and VII owing to the decrease in GAG accumulation at the intracellular level.

A. BRIEF DESCRIPTION OF THE DRAWINGS

FIG. 1—Odiparcil increases, in a dose-dependent manner, the level of $^{35}$S-labeled GAGs in the culture supernatant of bovine aortic endothelial cells.

Figure 2:
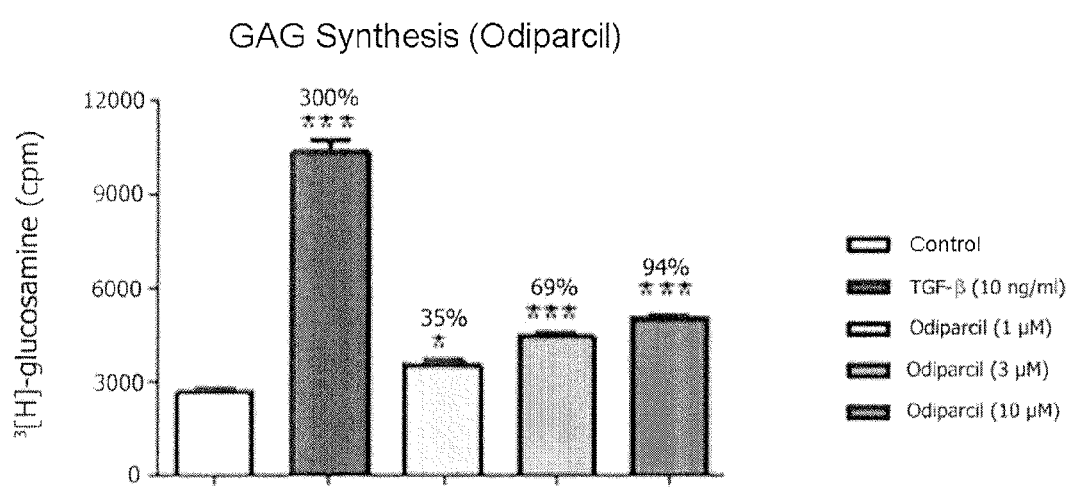

FIG. 2—Odiparcil stimulates, in a dose-dependent manner, total GAG synthesis by human dermal fibroblasts.

B. SUBJECT OF THE INVENTION

According to a first aspect, the invention relates to Odiparcil for use in the treatment of mucopolysaccharidosis type III, VI or VII, and in particular in the treatment of MPS type VI (also called Maroteaux-Lamy disease).

Odiparcil and the process for obtaining it are described in patent application EP-A-0 421 829.

In the context of the present invention, the term "Odiparcil" denotes the "β-D-xylopyranoside" form.

In one embodiment, the Odiparcil used in the context of the invention is at least 60%, preferably at least 70%, at least 80%, at least 90%, at least 95%, at least 98% or at least 99% in the D-configuration. In this embodiment, the Odiparcil is preferably in β-anomer form.

In another embodiment, the Odiparcil used in the context of the invention is at least 60%, preferably at least 70%, at least 80%, at least 90%, at least 95%, at least 98% or at least 99% in the β-anomer form.

Advantageously, the Odiparcil is administered in a proportion of approximately 100 mg to approximately 5000 mg per day. For example, approximately 100, 250, 300, 375, 400, 500, 750, 800, 1000, 1500, 2000, 3000, 4000 or 5000 mg of Odiparcil are administered daily.

In one embodiment, at least approximately 0.1 mg to approximately 70 mg of Odiparcil per kg of bodyweight of the patient are administered daily. For example, at least approximately 1 or 2 mg, to approximately 5, 10, 15, 20, 25, 30, 35, 40, 45, 50, 55, 60, 65 or 70 mg of Odiparcil per kg of bodyweight of the patient are administered daily.

In one embodiment, the Odiparcil is administered once or twice per day (for example, every 10 to 12 hours). Thus, the daily doses mentioned above can be divided up for a twice daily (bid) administration, for example a daily dose of 1000 mg will be administered in a proportion of two doses of 500 mg each. It is understood that each dose may consist of one or more pharmaceutical forms, for example a dose of 500 mg may consist of two pharmaceutical forms of 250 mg each.

In one embodiment, the Odiparcil is administered in a fasted state (i.e. on an empty stomach, for example at least 1 h before eating or more than 2 h after eating). In another embodiment, the Odiparcil is administered during a food intake (i.e. at the same time as or just before eating a meal, for example approximately 20 to 30 min before a meal or within 5 min following the end of a meal).

In one embodiment, the Odiparcil is formulated in a pharmaceutical composition containing one or more pharmaceutically acceptable excipients, according to techniques well known to those skilled in the art, for instance those described in the book "Remington, The Science and Practice of Pharmacy, 21st Edition, Lippincott Williams & Wilkins, 2006".

Thus, according to a second aspect, the invention relates to a pharmaceutical composition containing Odiparcil and one or more pharmaceutically acceptable excipients, for use in the treatment of mucopolysaccharidosis type III, VI or VII, in particular the treatment of Maroteaux-Lamy disease.

The pharmaceutical composition may be in any form suitable for the desired route of administration. This administration may be per os, lingual, sublingual, oral, rectal, topical, intravenous, intra-arterial, subcutaneous, intranasal, transdermal, intramuscular or intraperitoneal.

In one embodiment, the pharmaceutical composition contains approximately 100 to 1000 mg of Odiparcil, for example 100, 125, 150, 250, 375, 400, 500 or 1000 mg of Odiparcil.

In one embodiment, the pharmaceutical composition is administered by the injectable route, and comprises a vehicle which is typically a sterile aqueous solution sometimes containing, in addition to the water, one or more ingredients such as sugars, preservatives, salts, buffers, etc. The injectable suspensions may comprise a suspending agent and a given liquid vehicle.

In one embodiment, the pharmaceutical composition is administered orally. Suitable oral pharmaceutical forms include solid and liquid formulations. When the pharmaceutical composition is a solid formulation (such as, for example, gelatin capsules, tablets, dry powders), useful excipients include, in particular, diluents, lubricants, binders, disintegrating agents, fillers, etc. The solid formulations may be coated or uncoated; when they are coated, the coating may be enteric or nonenteric. When the pharmaceutical composition is a liquid formulation (such as, for example, an elixir or a syrup), the useful excipients include, for example, water, glycols, a saline solution, alcohols, flavoring agents, etc.

Advantageously, the pharmaceutical composition is a tablet. Such a composition is prepared in one or more steps, comprising the mixing of the various constituents until a homogeneous mixture is obtained, and the compressing of the mixture so as to obtain a tablet. In one embodiment, the composition is prepared by means of a wet granulation process, which is a technique well known to those skilled in the art. For example, the Odiparcil, all or part of the diluent, the binder and a sufficient amount of granulating fluid (such as water) are combined, granulated, dried and ground so as to form granules. The granules are then optionally combined with the rest of the constituents and the mixture is compressed. The tablets advantageously comprise approximately 5% to approximately 90% of Odiparcil, relative to the total weight of the tablet.

According to a third aspect, the invention relates to a method for treating mucopolysaccharidosis type III, VI or VII, in particular Maroteaux-Lamy disease, which consists in administering, to a subject in need thereof, a therapeutically effective amount of Odiparcil or of a pharmaceutical composition containing this compound. In one embodiment, the daily dosage regimen of Odiparcil and the pharmaceutical composition are as defined above.

The invention is illustrated by the experimental section below.

Pharmacological Activity

1. Results Obtained on Cells in Culture 1.1. Bovine Aortic Endothelial Cells

Bovine aortic endothelial cells (ECACC 92010601), cultured in 6-well plates, are incubated for 24 h in the presence of $^{35}$S sodium sulfate (10 µci/ml) and of Odiparcil solubilized in DMSO at various concentrations (1-10 µM; 0.1% final concentration of DMSO). The culture supernatants are recovered and the cell layers are rinsed with phosphate buffer (PBS). The culture supernatants and the rinsing solutions are combined in tubes. A solution of unlabeled dermatan sulfate (200 µg) is then added in order to serve as an entraining agent. The unincorporated $^{35}$S is then removed by gel filtration on Sephadex G25 columns, the GAGs being eluted in the column exclusion fraction (V0). A solution of cetylpyridinium chloride (0.1% final concentration) is added to the eluent in order to precipitate the GAGs for 24 h at room temperature. The samples are then centrifuged and the supernatant is removed. The precipitate obtained is redissolved in 2 M magnesium chloride and the GAGs are precipitated with 5 volumes of 95% ethanol. After centrifugation, the alcoholic precipitates are redissolved in 0.9% sodium chloride and then the radioactivity is measured on an aliquot fraction after addition of scintillation fluid in counting vials.

In order to type the GAGs produced in the supernatants from cells in culture, the redissolved alcoholic precipitates are treated with chondroitinase ABC (*Proteus vulgaris*) in a proportion of 0.5 mU/µL, for 3 h at 37° C. After inactivation of the enzyme for 3 min at 100° C., the undigested GAGs are precipitated with 5 volumes of 95% ethanol, overnight at 4° C. After centrifugation, the alcoholic precipitates are redissolved in 0.9% sodium chloride and then the radioactivity is measured on an aliquot fraction after addition of scintillation fluid in counting vials.

For GAGs of heparan sulfate type, they are treated with heparinase II (*Flavobacterium heparinum*) in a proportion of 4 mU/µl, for 12 h at 30° C. After inactivation of the enzyme for 3 min at 100° C., the undigested GAGs are precipitated with 5 volumes of 95% ethanol, overnight at 4° C. After centrifugation, the alcoholic precipitates are redissolved in 0.9% sodium chloride and then the radioactivity is measured on an aliquot fraction after addition of scintillation fluid in counting vials. As can be seen in FIG. 1, Odiparcil increases, in a dose-dependent manner, the level of $^{35}$S-labeled GAGs in the culture supernatant of bovine aortic endothelial cells. Furthermore, the enzymatic digestions suggest that the GAGs synthesized by the cells in culture are predominantly of chondroitin sulfate type.

1.2. Human Fibroblasts

Normal human dermal fibroblasts (BIOAlternatives PF2) are cultured in 96-well plates for 24 h. The culture medium is then replaced with culture medium containing or not containing (control) Odiparcil at various concentrations (1 µM, 3 µM, 10 µM) or the TGF-β reference at 10 ng/ml (positive control), and then the cells are incubated for 72 h with addition of the $^3$H-glucosamine radioactive label for evaluating total GAG synthesis. At the end of the incubation, a chaotropic buffer is added to the wells of the culture plates in order to lyse the fibroblasts. The total GAGs of the cell lysates are then purified by ion exchange chromatography (Q-Sepharose column). The radioactivity incorporated into the anionic fractions is measured by liquid scintillation.

As can be seen in FIG. 2, Odiparcil stimulates, in a dose-dependent manner, total GAG synthesis by human dermal fibroblasts (+94% at 10 µM). The data were analyzed statistically by one-way analysis of variance, followed by a Dunnett's test (* p<0.05 vs control;  p<0.01 vs control; * p<0.001 vs control).

2. Results Obtained In Vivo in Rabbits after Oral Administration

Odiparcil is administered orally to New Zealand rabbits at the dose of 400 mg/kg. 4 h after the administration, the animals are anesthetized and blood samples are taken on citrate tubes after catherization of the carotid artery. After centrifugation, the plasma is removed and frozen. The plasma GAGs are isolated after digestion of the proteins with Pronase E, for 48 h at 50° C. The proteins and the protein residues are precipitated by adding trichloroacetic acid and incubating overnight at 4° C. After centrifugation, the supernatants are collected, and then dialyzed against 100 volumes of phosphate buffer, for 48 h at 4° C. A solution of cetylpyridinium chloride (0.1% final concentration) is added to the dialysates in order to precipitate the GAGs, for 24 h at ambient temperature. The samples are then centrifuged and the supernatant is removed. The precipitate obtained is redissolved in 2M sodium chloride and the GAGs are precipitated with 5 volumes of 95% ethanol. After centrifugation, the alcoholic precipitates are redissolved in 0.9% sodium chloride and desalified on a Sephadex G25 column (PD10).

The plasma GAGs extracted are quantified by assaying the uronic acid content, modified Bitter and Muir carbazole method. The qualitative analysis of the plasma GAG extracts is carried out by HPLC of the disaccharides obtained after enzymatic digestion with chrondroitinase ABC from *Proteus vulgaris* and chrondroitinase AC from *Arthrobacter aurescens*.

The table below shows that the treatment of the animals with Odiparcil at the dose of 400 mg/kg increases by a factor of 5 the plasma GAG level (measured via the uronic acid content) compared with the control animals. From a qualitative point of view, the chondroitin-type GAGs experience an increase in their galactosamine-6-sulfate component and also in the dermatan sulfate component (chondroitin B), measured via the galactosamine-4-sulfate disaccharides (Δdi-4S DS).

| | µg UA/ml plasma | Δdi-0S (%) | Δdi-4S (%) | Δdi-6S (%) | Δdi-UA2S (%) | Δdi-4S DS (%) |
|---|---|---|---|---|---|---|
| Control | 2.1 | 51.1 | 45.8 | 3.1 | 0 | 0 |
| Odiparcil | 11.4 | 18.6 | 26 | 30.8 | 4.1 | 20.5 |

UA: Uronic acid
Δdi-0S: nonsulfated disaccharides
Δdi-4S: 4-sulfated disaccharides
Δdi-6S: 6-sulfated disaccharides (galactosamine-6-sulfate component)
Δdi-UA2S: 2UA-sulfated disaccharides
Δdi-4S DS: 4-sulfated disaccharides (dermatan sulfate component)

These results demonstrate that Odiparcil has the capacity to increase the synthesis of total GAGs (human fibroblasts), to increase the concentration of extracellular GAGs of chondroitin type (bovine aortic endothelial cells) and to increase the synthesis of plasma GAGs, in particular for GAGs of chondroitin type. It being understood that MPS type III, VI and VII are characterized by an accumulation of intracellular GAGs, these results indicate that Odiparcil has the capacity to decrease the intracellular GAG load and therefore to have beneficial effects in the treatment of said MPSs.

Example of Pharmaceutical Formulation

| Tablet obtained by means of a wet granulation process, containing (in weight %): | |
|---|---|
| Odiparcil | 90% |
| Microcrystalline cellulose (NF or Ph Eur) | 7% |
| Povidone or polyvinylpyrrolidone (USP or Ph Eur) | 3% |
| Water (USP or Ph Eur) | qs for wet granulation |

The invention claimed is:

1. A method of treatment of a mucopolysaccharidosis type VI or VII, which comprises administering to a subject in need thereof a therapeutically effective amount of odiparcil (4-methyl-2-oxo-2H-1-benzopyran-7-yl-5-thio-β-D-xylopyranoside).

2. The method of claim 1, which comprises the daily administration of from about 100 mg to about 5000 mg of odiparcil.

3. The method of claim 1, wherein odiparcil is administered orally.

4. The method of claim 3, wherein odiparcil is administered with food.

5. The method of claim 1, for the treatment of mucopolysaccharidosis type VI (Maroteaux-Lamy disease).

6. A method of treatment of a mucopolysaccharidosis type VI or VII, which comprises administering to a subject in need thereof a pharmaceutical composition containing a therapeutically effective amount of odiparcil (4-methyl-2-oxo-2H-1-benzopyran-7-yl-5-thio-β-D-xylopyranoside).

7. The method of claim 6, wherein the pharmaceutical composition contains from about 100 mg to about 1000 mg of odiparcil.

8. The method of claim 6, wherein the pharmaceutical composition is an oral pharmaceutical form, preferably a solid formulation.

9. The method of claim 8, wherein the pharmaceutical composition is a solid formulation.

10. The method of claim 8, wherein the pharmaceutical composition is a tablet.

11. The method of claim 6, for the treatment of mucopolysaccharidosis type VI (Maroteaux-Lamy disease).

* * * * *